United States Patent [19]

Kaplan et al.

[11] Patent Number: 5,196,555

[45] Date of Patent: Mar. 23, 1993

[54] WATER AND SOLVENT SOLUBLE AXIAL HYDROXY AND MONO- AND DI-CARBOXYLIC ACID DERIVATIVES HAVING HIGH TUMOR ACTIVITY

[75] Inventors: Murray A. Kaplan, Syracuse; Robert K. Perrone, Liverpool; Joseph B. Bogardus; Kenneth J. Wilcox, Syracuse, all of N.Y.

[73] Assignee: Bristol-Myers Squibb Company, New York, N.Y.

[21] Appl. No.: 808,262

[22] Filed: Dec. 13, 1991

Related U.S. Application Data

[63] Continuation of Ser. No. 661,714, Feb. 27, 1991, abandoned, which is a continuation of Ser. No. 422,843, Oct. 17, 1989, abandoned.

[51] Int. Cl.$^5$ .................. C07F 15/00; A61K 31/28
[52] U.S. Cl. ................................................ 556/137
[58] Field of Search ......................... 556/137

[56] References Cited

U.S. PATENT DOCUMENTS

| | | | |
|---|---|---|---|
| 4,119,653 | 10/1978 | Tobe et al. ............ | 556/137 X |
| 4,119,654 | 10/1978 | Tobe et al. ............ | 556/137 |
| 4,431,666 | 2/1984 | Bulten et al. .......... | 556/137 |
| 4,466,924 | 8/1984 | Verbeek et al. ........ | 556/137 |
| 4,581,224 | 4/1986 | Borch .................. | 556/137 |
| 4,594,238 | 6/1986 | Borch .................. | 556/137 X |
| 4,658,047 | 4/1987 | Vishnuvajjala ......... | 556/137 |
| 4,921,984 | 5/1990 | Nowatari et al. ....... | 556/137 X |
| 5,028,727 | 7/1991 | Verbeek et al. ........ | 556/137 |
| 5,034,553 | 7/1991 | Verbeek et al. ........ | 556/137 |

FOREIGN PATENT DOCUMENTS

| | | |
|---|---|---|
| 3282274 | 8/1989 | European Pat. Off. . |
| 2006213A | 5/1979 | United Kingdom . |
| 2148891A | 6/1985 | United Kingdom . |

OTHER PUBLICATIONS

Bondarenko, V. S., et al., Zh. Neorg. Khim., 1982, 27 (5):1234–1238 (Chem. Abst. 97:48589d) [Abstract Only].

Cowens, J. W., et al., Int. J. Mass. Spectrom. Ion Phys., 1983, (48):177–180 (Chem. Abst. 98:118519c) [Abstract Only].

Al-Ansari, S. V., Chem. Abst., 1984, 101:182625s [Abstract Only].

*Primary Examiner*—Arthur C. Prescott

[57] ABSTRACT

Platinum complexes are disclosed in which the formula is

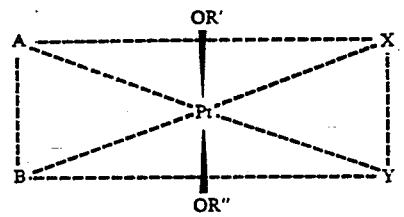

wherein A and B are each independently ammine or monodentate amine, or A and B taken together represent a bidentate amine, and A and B are coordinated to the platinum atom through their nitrogen atom; X and Y are each independently halogen; R' is $C_1$–$C_{20}$ alkanoyl, aroyl, heteroaroyl, or a group selected from the group consisting of

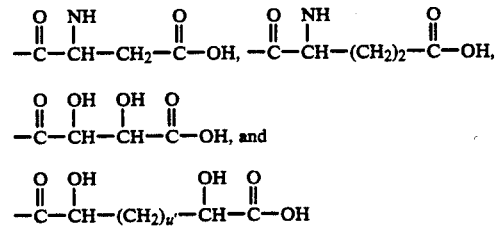

wherein u' is an integer from 1 to 5; and R" is hydrogen with the proviso that A, B, X, and Y are structually equatorial substituents with respect to OR'—Pt—OR". These platinum complexes show antitumor activity with relatively lower kidney or bone marrow toxicity.

17 Claims, No Drawings

WATER AND SOLVENT SOLUBLE AXIAL HYDROXY AND MONO- AND DI- CARBOXYLIC ACID DERIVATIVES HAVING HIGH TUMOR ACTIVITY

CROSS-REFERENCE TO RELATED APPLICATION

This application is a continuation of U.S. Ser. No. 661,714 filed Feb. 27, 1991, which is a continuation of U.S. Ser. No. 422,843 filed Oct. 17, 1989, both now abandoned.

BACKGROUND OF THE INVENTION

1. Field of the Invention

The invention relates to axial hydroxy and axial carboxylate platinum (IV) compounds which possess antitumor activity. Certain of the compounds of the present invention also possess excellent water-solubility which makes them more efficacious in pharmaceutical dosage form than known chemically effective platinum derivatives; other compounds are liposoluble which indicates their potential use in liposomes, for incorporating into the internal oil phase of an oil/water emulsion for oral or parenteral dosage forms, for injection as oil solutions directly into solid tumors, or for topical use in ointments, gels, and the like. The compounds according to the present invention demonstrate properties superior to other platinum compounds known in the art, such as lower kidney or bone marrow toxicity, as well as high tumor activity.

2. Description of the Prior Art

A large number of platinum II and platinum IV complexes have been evaluated for use as antitumor agents.

Many such derivatives have exhibited in vitro and in vivo activity against neoplastic cells. A platinum (II) compound (cis-dichlorodiammine platinum (II)) is commercially available for treatment of certain human tumors. However, most of these derivatives have undesired side effects when administered in vivo or are not very soluble in aqueous fluids.

Published patents, patent applications, and technical journal documents relating to platinum (IV) derivatives are as follows:

U.S. Pat. No. 4,466,924 relates to platinum compounds of the type

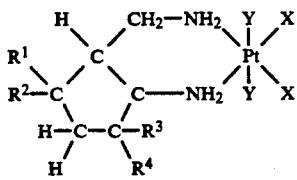

wherein X is halogenoid, a sulphate radical, a substituted carboxylate radical, or an unsubstituted carboxylate radical and Y is halogenoid, a hydroxyl group, a nitrate group, or acarboxylate. However, only tetra-halogen derivatives and dihalo-dihydroxy derivatives are shown as particular species compounds.

U.S. Pat. No. 4,250,189 relates to platinum compounds of the type

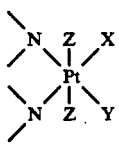

wherein Z is absent or is halogen, pseudohalogen (e.g., cyanide, cyanate, thiocyanate, and azide), or hydroxy. sulphate, phosphate, nitrate, carboxylate, substituted carboxylate, water, halogen, or pseudohalogen. No axial carboxylate derivatives are disclosed or claimed.

U.S. Pat. Nos. 4,581,224 and 4,594,238 relate to the process for using dithiocarbamic compounds to reduce harmful side effects caused by the administering of platinum complex compounds. Among other platinum compounds generally outlined at Page 11 in each of the above referenced patents were those compounds relating to the general formula

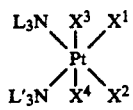

wherein a number of substituents for $X^1$, $X^2$, $X^3$, and $X^4$ are generally described, but halogen substituents were preferred for $X^1$ and $X^2$ and —OH or water molecules were preferred for $X^3$ and $X^4$. The platinum compounds are very generally and broadly set forth, and no examples of compounds or subgeneri are disclosed wherein the equatorial substituents are halogen when at least one of the axial substituents is a carboxylate derivative.

U.S. Pat. No. 4,119,654 relates to platinum compounds of the type

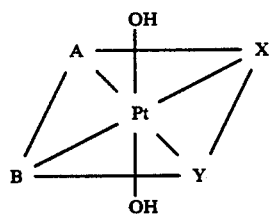

wherein X and Y are halogenoid and A and B each independently represent branched chain aliphatic amine groups having the formula

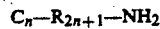

$$C_n-R_{2n+1}-NH_2$$

wherein n is an integer from 3–9 and wherein all of the R groups are the same or different and are selected from the group consisting of hydrogen, alkyl, aryl, alkanyl, aralkyl, halogen, pseudohalogen, hydroxy, carbonyl, formyl, nitro, amido, amino, sulfonic acid, sulfonic acid salt, carboxylic acid, and carboxylic acid salt.

U.S. Pat. No. 4,119,653 relates to platinum compounds of the type

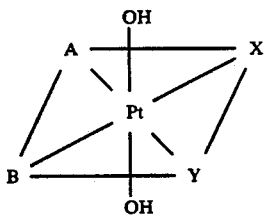

wherein X and Y are halogenoid and A and B each independently represent ammine (NH₃) or straight chain aliphatic amine groups having the formula

in which n is an integer from 3-9 and R is as defined in U.S. Pat. No. 4,119,654, referenced above.

U.K. Patent Application 2,006,213A relates to platinum compounds of the type

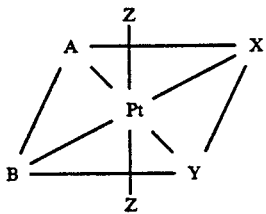

wherein inter alia, Z is hydroxy, X and Y are halogenoid, and A and B are alicyclic amine groups or C-substituted alicyclic amine groups of the formula

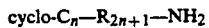

in which n=3-7 and R is as defined in U.S. Pat. No. 4,119,654, referenced above.

U.K. Patent Application 2,148,891A relates to compounds of the type

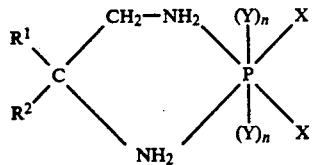

wherein $R_1$ and $R_2$ represent $C_1$-$C_3$ alkyl or jointly represent $C_3$-$C_6$ alkylene, X represents halogen,

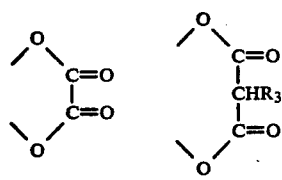

in which $R_3$ is lower alkyl or —OM, wherein M is monovalent cation; Y is OH or halogen; and n=0 or 1.

U.S. Pat. No. 4,658,047 relates to 1,2-diaminocyclohexane tetrachloro platinum (IV) isomers of the type

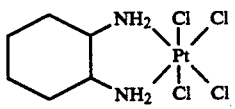

wherein the compounds are cis-, trans (d,l), trans-1, or trans-d.

U.S. Pat. No. 4,431,666 relates to compounds of the type

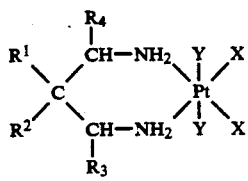

wherein $R_1$ and $R_2$ are each independently hydrogen or an alkyl, aryl, or aralkyl group having 1-20 carbon atoms or a cycloalkyl group having 3-7 carbon atoms, while $R_1$ and $R_2$ together may be a cycloalkyl group having 3-7 carbon atoms, $R_3$ and $R_4$ are each independently hydrogen or alkyl, aryl or aralkyl groups having 1-20 carbon atoms, and X and Y are each independently an anionic group.

Some acylated platinum (IV) derivatives are described in the literature. For example, Zh. Neorg. Khim 27 (5): 1234–1238, 1982, relates to a platinum complex of the formula

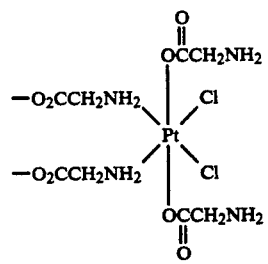

Int. J. Mass. Spectrom. Ion. Phys., 48, 177–180, 1983, relates to platinum complexes of the formulae

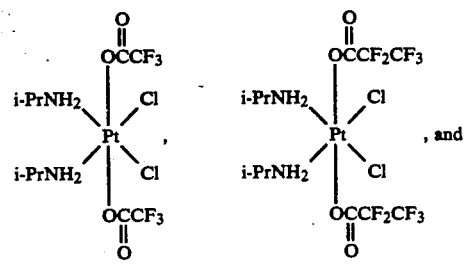

-continued

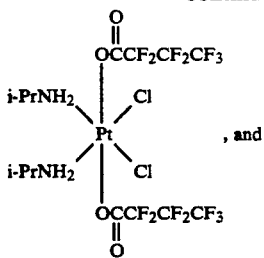, and

*Chemical Abstracts* 101 (20): 182625s relates to platinum complexes of the formula

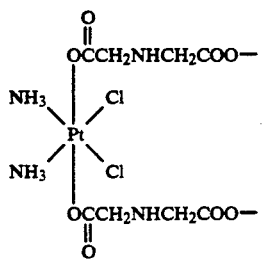

SUMMARY OF THE INVENTION

Axial hydroxy and axial carboxylate compounds have been discovered which have the formulae

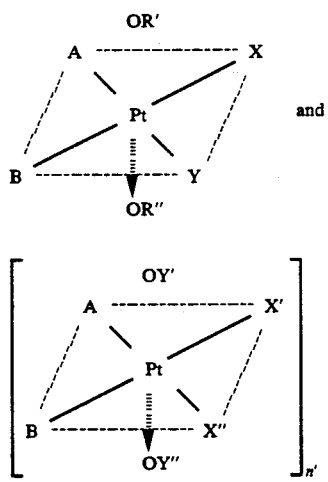

wherein for Formula I, A and B are each independently ammine or monodentate amine, or A and B taken together represent a bidentate amine, and A and B are coordinated to the platinum atom through their nitrogen atom; X and Y are each independently halogen; and R' and R" are each independently hydrogen, $C_1$-$C_{20}$ alkanoyl, aroyl, heteroaroyl, or a group selected from the group consisting of

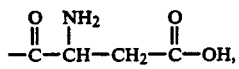

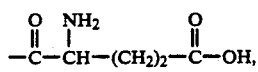

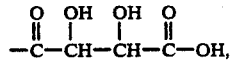

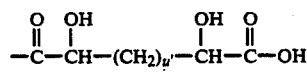

wherein u' is an integer from 1 to 5; with the proviso that one of R' and R" is other than hydrogen and with the further proviso that A, B, X, and Y are structurally equatorial substituents with respect to OR'-Pt-OR", and wherein, for Formula Ia, A and B are each independently ammine or monodentate amine, or A and B together represent a bidentate amine; n' is 1 or 2, and when n' is 1, one of X' and X" is halo and the other is $C_1$-$C_{10}$ acyloxy, Y' and Y" each independently represent $C_1$-$C_{10}$ acyl, with the proviso that A, B, X', and X" are structurally equatorial substituents, and when n' is 2, X' and X" are each independently halo; at least two of the four available Y' and Y" groups are bridged by a dicarboxylic acid derivative group to form a dimer and the bridging group is selected from the group consisting of

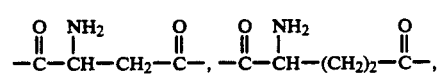

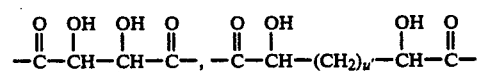

wherein u' is an integer from 1 to 5; and the remaining Y' and Y" groups are independently hydrogen, $C_1$-$C_{10}$ alkanoyl, aroyl or heteroaroyl with the proviso that the A, B, X', and X" groups are structurally equatorial substituents with respect to OY'-Pt-OY".

The terms "equatorial" and "axial" are being used throughout the present application to represent the three-dimensional steric relationship of the substituents attached to the platinum (IV) core relative to one another in the same platinum metal complex. Thus, for example, in Formula I, (A,B)=Pt=(X,Y) form an equatorial plane "with respect to an axial plane formed by OR'-Pt-OR".

Surprisingly, compounds according to the present invention have been found to be useful in the treatment of tumors. Namely, the platinum complexes according to the present invention possess potent antitumoral activity and thus are useful in the therapeutic treatment of mammals and other animals for diseases caused by tumors to inhibit the growth of mammalian tumors. The compounds of the present invention, therefore, are useful in a method for therapeutically treating an animal host affected by a malignant tumor which comprises administering to said host an effective tumor-inhibiting dose of a compound according to the present invention, or a pharmaceutical composition thereof.

Accordingly, in an additional aspect, compounds of the present invention are useful in a pharmaceutical composition which comprises an effective tumor-inhibiting amount of a compound according to the present invention in combination with an inert pharmaceutically acceptable carrier or diluent.

Physical properties of compounds according to the present invention are particularly suited for treating tumors. For example, the shorter carbon number acylated derivatives are usually water soluble, and some of the compounds are highly water soluble. Those compounds having excellent water-solubility are more efficacious in pharmaceutical dosage form than known chemically effective platinum derivatives, e.g., intravenous solutions, injectable solutions, and oral compositions.

Surprisingly, the higher carbon number acylated derivatives are usually oil soluble, and there are advantages for these compounds which are oil and/or liposoluble since they are very well suited for incorporating into liposomes, or the internal oil phase of an oil/water emulsion for oral or parenteral dosage forms. They are also useful for injection as oil solutions directly into solid tumor; or for topical use in ointments, gels, etc.

DESCRIPTION OF THE PREFERRED EMBODIMENT

The compounds, according to the present invention, are useful as anti-tumoral agents as indicated in the above summary. However, certain subgenera and species are more preferred embodiments of the invention. These more preferred compounds and subgenera are set forth below.

Preferred compounds according to the present invention are those compounds having the formula

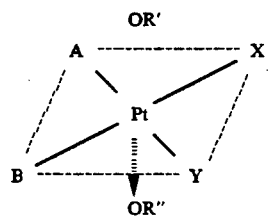
(I)

wherein A and B are each independently ammine or a $C_3$-$C_7$ alicyclic amine group coordinated to the platinum atom through their nitrogen atom.

Also preferred are compounds according to Formula I wherein A and B are taken together to form a $C_3$-$C_7$ alicyclic diamino group. Even more preferred are compounds thus subsituted wherein A and B taken together represent 1,2-diamino-cyclohexane, especially cis-, trans (d,l)-, trans (1), or trans (d)- 1,2-diamino-cyclohexane.

Also preferred are compounds of Formula I wherein A and B each independently represent ammine or a straight or branched chain aliphatic amine group having from 1 to 6 carbon atoms and being coordinated to the platinum atom through their nitrogen atom. Particularly preferred among compounds thus substituted are compounds having the formula

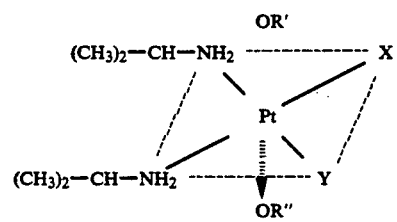
(II)

wherein X and Y are each independently halogen and R' and R" are each independently hydrogen, $C_1$-$C_{20}$ alkanoyl, benzoyl, or nicotinoyl with the proviso that one of R' and R" is other than hydrogen and with the further proviso that A, B, X, and Y are structurally equatorial substitutuents with respect to OR'-Pt-OR".

Even more preferred are compounds of the Formula II type having the following structures:

formula
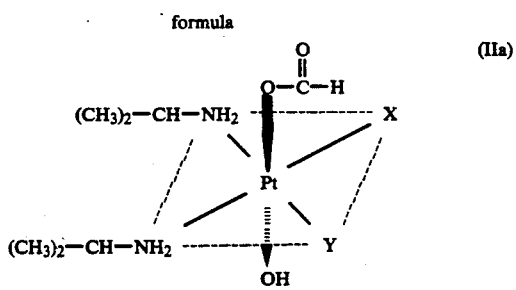
(IIa)

formula
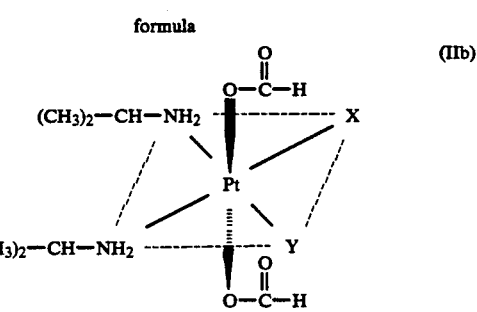
(IIb)

formula
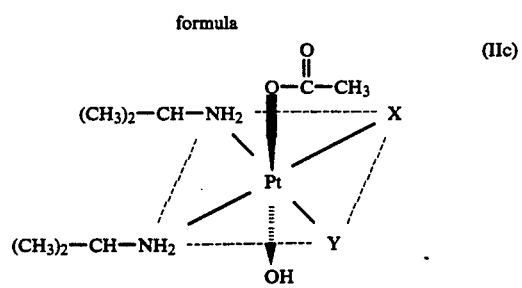
(IIc)

formula
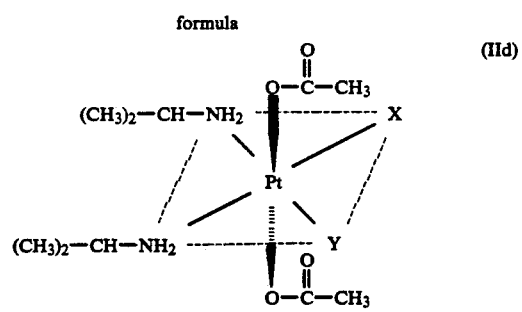
(IId)

formula
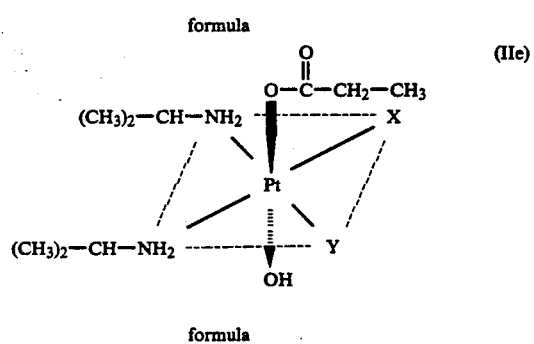
(IIe)

formula

-continued

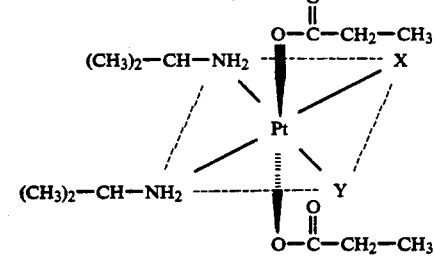

formula (IIf)

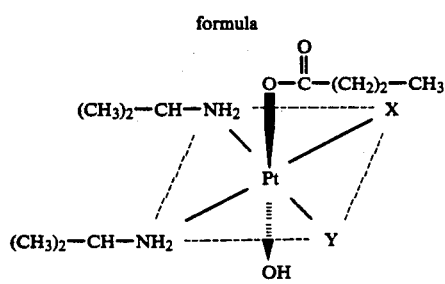

formula (IIg)

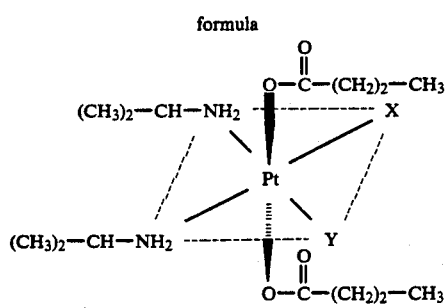

formula (IIh)

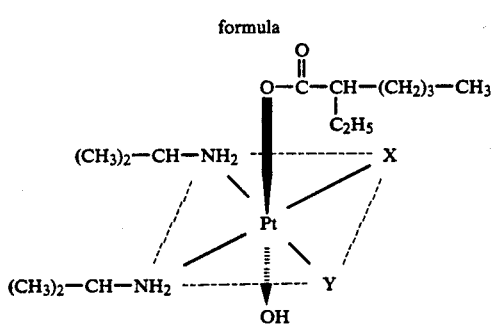

formula (IIi)

and formula (IIj)

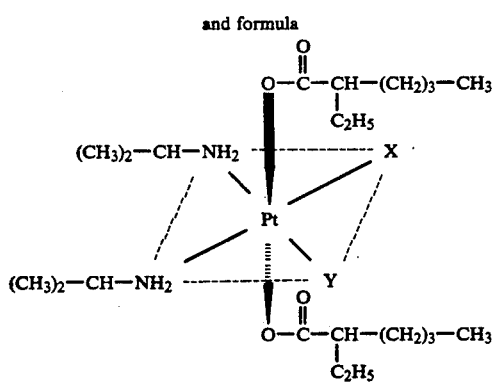

Also preferred are compounds represented by the formula

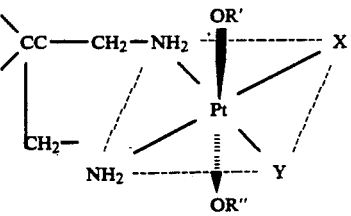
(III)

in which $R_1$ and $R_2$ each independently represent a hydrogen atom, $C_1$-$C_6$ alkyl, $C_3$-$C_7$ cycloalkyl, $C_6$-$C_{10}$ aryl, or $C_1$-$C_6$alkyl, or $R_1$ and $R_2$ taken together with the carbon atom to which they are attached represent $C_3$-$C_7$cycloalkyl; R' and R" are each independently hydrogen, $C_1$-$C_{20}$alkanoyl, benzoyl, or nicotinoyl with the proviso that one of R' and R" is other than hydrogen and with the further proviso that A, B, X, and Y are structurally equatorial substituents with respect to OR'-Pt-OR". Particularly preferred among compounds thus substituted are compounds wherein X and Y are each chloro. Even more preferred are compounds of this type wherein $R_1$ and $R_2$ each represent $CH_3$-$CH_2$13 or wherein $R_1$ and $R_2$ taken together with the carbon atom to which they are attached represent

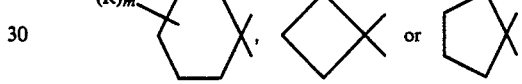

wherein each R is independently halogen or $C_1$-$C_6$ alkyl and m is an integer from 0 to 10.

Further preferred are compounds of the Formula III type wherein R is $C_1$ to $C_5$ alkyl and m is an integer from 0 to 10, which have the formula

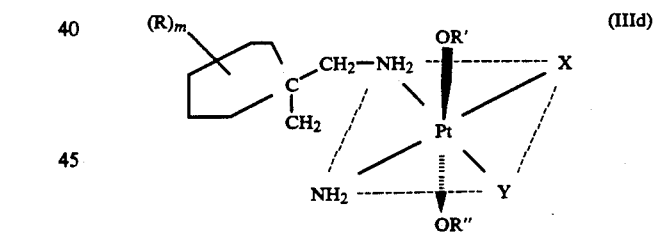
(IIId)

the X, Y, R', and R" substituents are as in Formula III, above. Particularly preferred is a compound wherein X and Y are each chloro, R' is —C(=O)—CH$_3$, R" is H, and m is O, or a compound wherein X and Y are each chloro, R' and R" are each —C(=O)—CH$_3$, and m is O.

Still further preferred are compounds of the Formula III type which have the formula

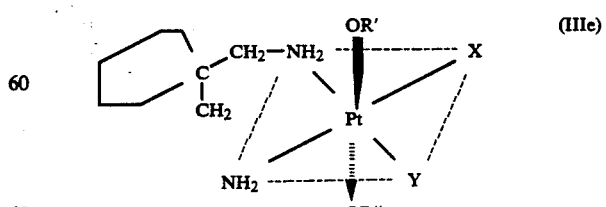
(IIIe)

wherein the X, Y, R', and R" substituents are as in Formula III, above.

Also preferred are compounds represented by the formula

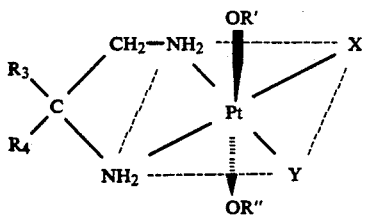
(IIIf)

wherein $R_3$ and $R_4$ each represent $C_1$–$C_6$ alkyl or $R_3$ and $R_4$ taken together with the carbon to which they are attached represent $C_3$–$C_7$ cycloalkyl; $R'$ and $R''$ are each independently hydrogen, $C_1$–$C_{20}$ alkanoyl, benzoyl, or nicotinoyl with the proviso that one of $R'$ and $R''$ is other than hydrogen and the further proviso that A, B, X, and Y are structurally equatorial substituents with respect to O$R'$-Pt-O$R''$.

Also preferred are compounds according to Formula Ia when n' is 1, which have the formula

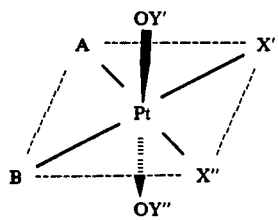
(IV)

wherein A and B are each independently ammine or a $C_3$–$C_7$ alicyclic group coordinated to the platinum atom through their nitrogen atoms, wherein one of $X'$ and $X''$ is chloro and the other is $C_1$–$C_{10}$ acyloxy; $Y'$ and $Y''$ are each $C_1$–$C_{10}$ acyl. Particularly preferred among compounds thus substituted are compounds wherein one of $X'$ and $X''$ is chloro and the other is a 2-ethyl-hexanoyl group. Also preferred among compounds thus substituted are compounds wherein $Y'$ and $Y''$ are each a 2-ethyl-hexanoyl group. Even more preferred among compounds thus substituted are compounds wherein the halo group is chloro.

Also preferred are compounds according to Formula Ia when n' is 2, wherein A and B are each independently ammine, a $C_1$–$C_5$ aliphatic amine, or a $C_3$–$C_7$ alicyclic amine group coordinated to the platinum atoms through their nitrogen atoms, wherein $X'$ and $X''$ are chloro.

Further preferred are compounds according to Formula I wherein X and Y are both chloro; $R'$ is a substituent selected from the group consisting of formyl, acetyl, propionyl, butanoyl, pentanoyl, hexanoyl, 2-ethyl-hexanoyl, heptanoyl, octanoyl, nonanoyl, decanoyl, and 2,3-dihydroxy-4-carboxy-1-butanoyl; $R''$ is a substitutent selected from the group consisting of hydrogen, formyl, acetyl, propionyl, butanoyl, pentanoyl, hexanoyl, 2-ethylhexanoyl, heptanoyl, octanoyl, nonanoyl, decanoyl, and 2,3-dihydroxy-4-carboxy-1-butanoyl; and A and B are both isopropylamine, or A and B taken together represents a group selected from the group consisting of 1,2-diaminopropane, 1,1-bis(aminomethyl)cyclobutane, 1,1-bis(aminomethyl)cyclopentane, 1,1-bis(aminomethyl)cyclohexane, and 1,2-diaminocyclohexane with the proviso that A, B, X, and Y groups are structurally equatorial substituents with respect to O$R'$-Pt-O$R''$.

Compounds according to the present invention having the structures of Formulae I and Ia can be made by acylating the corresponding intermediate compounds comprising hydroxy groups (or protected hydroxy groups, such as hydroxy groups which have been acylated, placed in a salt form with a metallic ion (such as the sodium salt), and the like), followed by separation and/or purification of the resulting acyl derivative compounds. For example, the intermediate compounds can be dissolved in an appropriate carboxylic acid and the solution may optionally contain a solvent suitable for both the intermediate compounds and the carboxylic acid; or the intermediate compounds may be acylated with a carboxylic acid derivative, such as an acyl halide or an anhydride, which are capable of acylating the hydroxy groups of the intermediates. Further substituents of carboxylic acid derivatives may be added or replaced by use of conventional methods, such as by transesterification procedures.

The reaction scheme is as follows:

Reaction Scheme 1

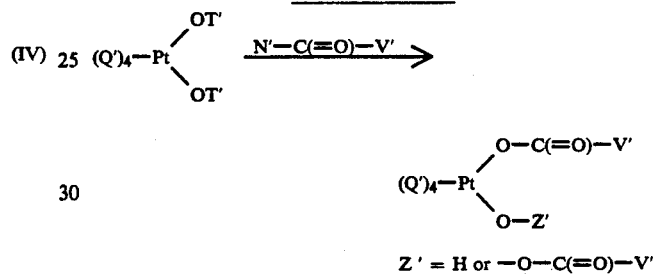

$Z' = $ H or $-$O$-$C($=$O)$-$V' wherein $(Q')_4$ relates to multiple non-reactive or protected groups also complexed with the Pt core; T' is a hydrogen atom or a leaving group, i.e., an acyl group, a metallic salt ion, and the like; and N'—C($=$O)—V' is the residue of a carboxylic acid wherein N' is an appropriate leaving group, i.e., an —OH group, a halo group, an anhydride group derivative, and the like.

More particularly, the compounds according to the invention can be made by following the general procedure as outlined below wherein the intermediate [equatorial]-dichloro[axial]-dihydroxy-diisopropylamine platinum (hereinafter, "3D-Pt"), or another appropriate [equatorial]-dichloro-[axial]dihydroxy-(ammine, monodentate amine or bidentate amino) platinum intermediates of about one gram in weight can be dissolved in about 10–50 milliliters of acid and stored in the dark at about 15° C.–95° C. for up to about 5 weeks, preferably at 25° C. for about 1 to 3 weeks or at about 50° C.–70° C. for about 1 day to 1 week.

The solution can optionally be monitored analytically during the reaction by High Pressure Liquid Chromatography (HPLC) and/or Thin Layer Chromatography (TLC) (e.g., a BOWMAC chromatographic instrument, Bridgewater, N.J.). At about 25° C. for one to three weeks, mono and di-esters form with the mono-ester predominating. However, at extended times or at the higher temperatures for shorter periods of time, the di-ester seems to predominate. Subsequently, the excess acid or acyl derivative reactant can be removed by vacuum at about 25° C. to 60° C. in a vacuum distilling apparatus, e.g., in a ROTOVAPOR apparatus (Brinkmann Instruments Company, which is a division of Sybron Corp., Cantiague Road, Westbury, N.Y.), preferably at a bath temperature of 35° C.–40° C. The residue is then worked up to concentrate and/or purify the resulting compounds.

For example, the residue is extracted with about 35-200 milliliters of an appropriate solvent for about 0.25-2 hours, preferably with 50-100 milliliters of ethyl ether for 0.5-1 hour. The crystalline mono-ester (Cr-1) can be collected at this point by filtration while saving the solvent filtrate (F-1), which is set aside for future work-up procedures. The above collected crystals (Cr-1) can be further worked up by washing with an appropriate solvent, e.g., 25 milliliters of ethyl ether to yield crystals (Cr-2), and the solvent filtrate (F-2) can be added to the prior solvent filtrate (F-1) to yield a solvent filtrate mixture (F-3).

The crystals (Cr-2) obtained by the above filtration can be optionally further purified, for example, washed with 25 milliliters of an appropriate solvent, such as a solvent comprising a mixture of lower alkanes and naphtha, e.g., SKELLYSOLVE-B (a mixture of hexanes, heptanes, octanes, and solvent naphtha, available from Skelly Oil Company), followed by vacuum drying the crystals at about 30° C.-65° C., preferably at 40° C.-50° C. for up to about 24 hours. The mono-ester derivative can then be obtained.

The F-3 solvent mixture can optionally be worked up by concentrating the mixture under vacuum, e.g., ROTOVAPOR apparatus, preferably at 35° C.-45° C. The compounds obtained can then be optionally further purified, e.g., by tituration with about 50 milliliters of SKELLYSOLVE-B, at about 25° C. and for about 2 hours while agitating.

The diester derivatives can be collected by filtration and then optionally further purified by washing with an additional 20 milliliters of a washing agent, e.g., SKELLYSOLVE-B, followed by vacuum drying the crystals at about 30° C.-65° C., preferably at 40° C.-50° C. for up to about 24 hours. The di-derivatives can then be obtained.

Moreover, it can be readily shown that the compounds according to the present invention are useful as agents for treating tumors. Physical properties of the compounds, according to the present invention, are particularly suited for treating tumors. For example, the shorter carbon number acylated derivatives are usually water soluble and soluble in solvents, such as lower alcohols, e.g., ethanol and the like, and compound examples 1-4, whose structures are as shown above, are highly water soluble and highly soluble in alcohol solvents and the like. The compounds having excellent water-solubility are potentially more efficacious in pharmaceutical dosage form than known chemically effective platinum derivatives, e.g., intravenous solutions, injectable solutions, and oral compositions.

Further, there are advantages for the other compounds which are oil and/or liposoluble since they are very well suited to be quite useful in liposomes, for incorporating into the internal oil phase of an oil/water emulsion for oral of parenteral dosage forms, for injection as oil solutions directly into solid matter, or for topical use in ointments, gels, etc. The di-propionate, the butyrate, and 2-ethylhexanoate esters are particularly preferred for these oil solutions.

The oil soluble compounds are useful for:
a) incorporation into the lipid-phase of liposomes;
b) incorporation into the internal oil-phase of oil/water emulsions for intravenous, intramuscular, intraperitoneal, and oral use;
c) injections of oil solutions directly into solid tumors;
d) injection of oil solutions intraperitoneal;
e) targeting to fatty tissues, lipomas, transport through fatty membranes; and
f) topical use of oil solutions as it is or by incorporating further as part of oil or lipid-phase ointments, gels, etc.

The surprisingly useful biological properties of compounds according to the present invention are readily evaluated in in vitro cytotoxicity assays, as well as in in vivo tumor models.

In Vitro Cytotoxicity

The cytotoxic activity of the platinum complexes were evaluated in vitro using B16-F10 murine melanoma cells and HCT-116 human colon carcinoma cells. The B16-F-10 cell line was maintained cultured in Eagle's Minimum Essential Medium (MEM) with Earle's salts (Gibco; Grand Island, N.Y.) enriched with 2 millimoles of L-glutamine, 2.06 millimoles of sodium pyruvate, insulin (0.26 units/ml), penicillin/streptomycin (10 units/milliliter and 10 micrograms/milliliter, respectively), MEM non-essential amino acids (0.6% Gibco; Grand Island, N.Y.), and 10% fetal bovine serum (Hyclone; Logan, Utah). The HCT-116 cells were grown in McCoy's 5A medium (modified, Gibco; Grand Island, N.Y.) supplemented with 2 millimoles of L-glutamine, 0.12 millimoles of L-serine, 0.17 millimoles of asparagine, 1.5 millimoles of sodium pyruvate, MEM essential amino acids (0.67%, Gibco; Grand Island, N.Y.), MEM vitamins (0.6%, Gibco; Grand Island, N.Y.), fetal calf serum (10%, Hyclone; Logan, Utah), and penicillin/streptomycin (10 units/milliliter and 10 micrograms/milliliter, respectively). Both cell lines were incubated at 37° C. in 5% $CO_2$/balance air high-humidity incubator.

Logarithmically growing cells were then harvested by mild trypsinization, and 4000 cells were added to each well of a 96-well microtiter plate (Costar; Cambridge, Mass.). The plates were incubated at 37° C. in 5% $CO_2$ overnight to permit cell attachment to the plate. The cells were then treated with a platinum complex according to the present invention, cisplatin, or iproplatin and then incubated for 72 hours. After incubating, the plates were inverted and shaken to remove media, drug, and detached cells. Formalin (10%) in phosphate buffered saline was added and the cells fixed for 10 minutes. The fixative was then removed, the plates air dried, stained with 0.0075% crystal violet for 15 minutes, washed twice, and air dried. The stain is solubilized with 0.2 milliliters of 0.2 Molar AcOH/EtOH (1:1) and optical densities determined using a Dynatech MR600 microtiter plate reader (Dynatech; Chantilly, Va.). IC50 values are calculated by linear regression analysis of absorption data.

Activity Against L1210 Murine Leukemia

The platinum complexes according to the present invention were tested for antitumor activity against L1210 murine leukemia. CDF1 mice weighing 20 grams were inoculated intraperitoneally or intracerebrally with $10^6$ or $10^5$ ascites cells of L1210 leukemia, respectively.

Drug administration was initiated the day following intra-peritoneal tumor implantation or 3 days following intracerebral implant. The complexes were administered at various dose levels by intraperitoneal injection. Groups of 4 to 6 mice were used for each dose level, and they were treated with a single dose of the complex on the treatment day. A group of 10 saline treated control mice were included in each experiment. Cisplatin and iproplatin treated groups were included as positive controls in each experiment.

The mice were weighed before treatment and again on day 5 or 6, and the average weight change was used as a measure of toxicity. The animals were observed daily for mortality, and the experiments terminated after 30 days. Antitumor activity was determined based on percent T/C, which is the ratio of the median survival time of the drug treated group to the median survival time of the saline treated control group times 100.

The saline treated mice usually had a median survival time of 7 days. A complex was considered active if it produced a T/C greater than or equal to 125 percent.

Activity Against M5076 Sarcoma

Platinum complexes according to the present invention were additionally evaluated for further antitumor activity against M5076 sarcoma. BDF1 mice, 8 per group, were inoculated subcutaneously with a fragment of M5076 sarcoma.

Intraperitoneal or intravenous treatment with the complexes was initiated 5 days after implant and was continued on days 9, 13, and 17 for a total of 4 treatments. From 4 to 6 doses were tested for each compound under study.

A saline treated control group and cisplatin treated groups were included in each experiment. The mice were observed daily for survivors, and the experiments terminated after 75-80 days.

The saline treated control mice exhibited a median survival time of 44.5 days to 50 days. Antitumor activity was determined based on a) median survival time of the drug treated mice relative to that of the controls (percent T/C) and b) the median time for tumors to reach 1 gram in drug treated mice relative to the controls (T-C). A complex was considered active if it produced a T-C greater than or equal to 13 days.

Activity Against P388 Murine Leukemia

The platinum complexes according to the present invention were tested for antitumor activity against P388 murine leukemia. CDF1 mice weighing 20 grams were inoculated intravenously with $10^6$ ascites cells of P388 leukemia.

Drug administration of the platinum complexes was initiated on the day following the intravenous tumor inoculation. The complexes were administered at various dosage levels by oral gavage. Groups of 6 mice were used for each dose level, and they were treated with a single dose of the complex on the treatment day. A group of 10 saline treated control mice were included in each experiment. Cisplatin treated groups were included as positive controls in each experiment.

The mice were weighed before treatment and again on day 5 or 6, and the average weight change was used as a measure of toxicity. The animals were observed daily for mortality, and the experiments terminated after 30 days. Antitumor activity was determined based on percent T/C, which is the ratio of the median survival time of the drug treated group to the median survival time of the saline treated control group times 100.

The saline treated mice usually had a median survival time of 7 days. A complex was considered active if it produced a T/C greater than or equal to 125 percent.

Drug Composition Preparation and Method of Use

For the above described in vitro cytotoxicity studies, the compounds are dissolved or suspended, depending on their solubility, in 0.9% Sodium Chloride or 10% ethanol in 0.9% Sodium Chloride. The compounds are prepared for in vivo treatment by dissolving or suspending in water (minimal amounts of Tween 80), 0.9% Sodium Chloride, or 10% ethanol in 0.9% Sodium Chloride. Olive oil or cotton seed oil are used for in vivo studies when the compounds are oil soluble compounds (see, for example, in Table 8, an oil soluble compound in olive oil, Example 9 (2-ethylhexanoate derivative), below).

The platinum complexes according to the present invention possess potent antitumoral activity (see, for example, Tables 7-9, below). Thus, the compounds according to the present invention are useful in the therapeutic treatment of mammals and other animals for diseases caused by tumors because of their ability to inhibit the growth of mammalian tumors.

The present invention, therefore, provides a method for therapeutically treating an animal host affected by a malignant tumor which comprises administering to said host an effective tumor-inhibiting dose of a compound according to the present invention as set forth above, or a pharmaceutical composition thereof.

In an additional aspect, the present invention provides a pharmaceutical composition which comprises an effective tumor-inhibiting amount of a compound according to the present invention, as set forth above in combination with an inert pharmaceutically acceptable carrier or diluent. These compositions may be made up in any pharmaceutical form appropriate for the mode of administration, as set forth above.

Preparations, according to the present invention, or pharmaceutical administration include sterile aqueous or non-aqueous solutions (e.g., oil or alcohol), suspensions, or emulsions. They may also be manufactured in the form of sterile solid compositions which can be dissolved in an appropriate solvent, such as sterile water, physiological saline, alcohol, PEG-400, oil, etc., or some other sterile medium suitable for topical, oral, or injectable administration, prior to use of the composition.

It will be appreciated that the actual preferred amounts of the platinum complexes to be used will vary according to the particular component, the particular composition formulated, the mode of application, and the particular situs, host, and disease being treated. Many factors that modify the action of the drug will be taken into account by those skilled in the art, for example, age, body weight, sex, diet, time of administration, route of administration, rate of excretion, condition of the host, rug combinations, reaction sensitivities, and severity of the disease. Administration can be carried out continuously or periodically within the maximum tolerated dose. Optimal application rates for a given set of conditions can be ascertained by those skilled in the art using conventional dosage determination tests in view of the above guidelines.

The following non-limiting examples for producing compounds, according to the present invention, and examples for demonstrating utility are provided.

EXAMPLE 1

Five hundred milligrams of [equatorial]-dichloro-[axial]-dihydroxy-diisopropylamine platinum "3D-Pt"

complex were dissolved in 10 milliliters of formic acid and stored in the dark at 25° C. for 1 week. The excess acid was then removed in a ROTOVAPOR apparatus at 35° C.–40° C. followed by dissolving the residue from the vacuum process in 10 milliliters of acetone and filtering the mixture. The filtrate was then extracted with 100 milliliters of ethyl ether, and the crystalline mono-formic acid ester derivative (formate) was then collected by filtration (Cr-1). The ether filtrate (F-1) was set aside for optional further work-up and/or purification, and the crystals (Cr-1) were washed with 15 milliliters of ether, whereupon the wash liquid (F-2) was added to the F-1 mixture to form a mixture (F-3). The Cr-1 mono-ester crystals were washed with 25 milliliters of SKELLYSOLVE-B followed by vacuum drying of the crystals at 40° C.–50° C. for 24 hours. The yield was about 430 milligrams of substantially pure mono-formic acid ester derivatives of 3D-Pt having the formula

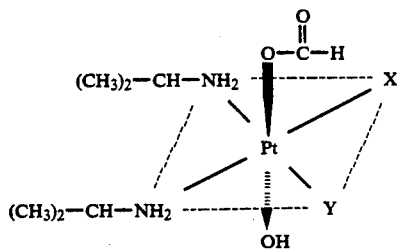
(IIa)

EXAMPLE 2

One hundred milligrams of 3D-Pt were dissolved in 4 milliliters of formic acid and stored in the dark for 1 week, and a precipitate which had formed was filtered off and set aside. The excess formic acid was removed via a ROTOVAPOR apparatus at 50° C. under vacuum, and the residue was extracted with 15 milliliters of acetone followed by evaporation of the acetone via the ROTOVAPOR apparatus. Subsequently, the residue was slurried in 20 milliliters of ethyl ether, and a crystalline solid was collected by filtration. The crystalline solid was dried at 50° C. under vacuum for 24 hours to yield 70 milligrams of a compound corresponding to formula

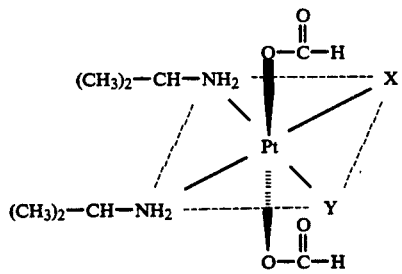
(IIb)

EXAMPLE 3

Six hundred and fifty milligrams of 3D-Pt were added to 20 milliliters of glacial acetic acid, and the mixture was stirred for 2 hours. The mixture was stored for 10 days at 25° C. in the absence of light and then worked up as in Example 1, above. The procedure yields about 550 milligrams of a compound according to formula

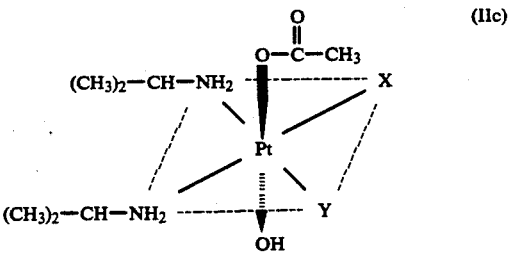
(IIc)

EXAMPLE 4

Six hundred and fifty milligrams of 3D-Pt were added to 20 milliliters of glacial acetic acid, and the mixture was stirred for 2 hours followed by 3 days at 70° C. in the absence of light. After being worked up using substantially the work-up procedures as in Example 2, above, the mixture yielded about 500 milligrams of a compound according to formula

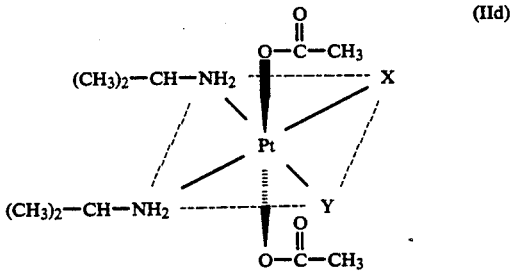
(IId)

EXAMPLE 5–10

The compound examples 5–10 having the formula

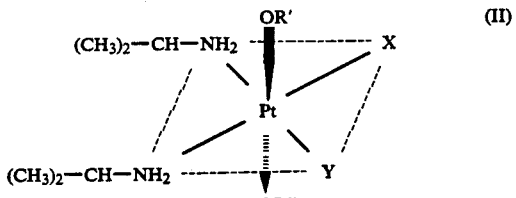
(II)

which are substituted as listed below at Table 1, were produced by following the procedures in Example 1–4 and reacting the corresponding carboxylic acid derivative with 3D-Pt.

TABLE 1

| Ex. No. | X | Y | R' | R" |
|---|---|---|---|---|
| 5 | —Cl | —Cl | $-\text{C}(=\text{O})-\text{CH}_2-\text{CH}_3$ | —H |

TABLE 1-continued

| Ex. No. | X | Y | R' | R" |
|---|---|---|---|---|
| 6 | —Cl | —Cl | —C(=O)—CH₂—CH₃ | —C(=O)—CH₂—CH₃ |
| 7 | —Cl | —Cl | —C(=O)—(CH₂)₂—CH₃ | —H |
| 8 | —Cl | —Cl | —C(=O)—(CH₂)₂—CH₃ | —C(=O)—(CH₂)₂—CH₃ |
| 9 | —Cl | —Cl | —C(=O)—CH(C₂H₅)—(CH₂)₃—CH₃ | —H |
| 10 | —Cl | —Cl | —C(=O)—CH(C₂H₅)—(CH₂)₃—CH₃ | —C(=O)—CH(C₂H₅)—(CH₂)₃—CH₃ |

EXAMPLE 11-23

Also by way of examples for practicing the present invention, the compounds according to Examples 11-23, having the formula

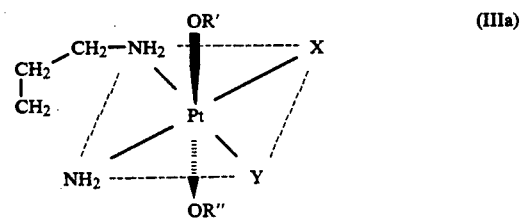

(IIIa)

which are substituted as listed below at Table 2 can be produced by substantially following the above outlined procedures to react the appropriate carboxylic acid derivatives with the appropriate axial-dihydroxy platinium complexes to yield compounds of Examples 11-23.

TABLE 2

| Ex. No. | X | Y | R' | R" |
|---|---|---|---|---|
| 11 | —Cl | —Cl | —C(=O)—H | —H |
| 12 | —Cl | —Cl | —C(=O)—H | —C(=O)—H |
| 13 | —Cl | —Cl | —C(=O)—CH₃ | —H |
| 14 | —Cl | —Cl | —C(=O)—CH₃ | —C(=O)—CH₃ |
| 15 | —Cl | —Cl | —C(=O)—CH₂—CH₃ | —H |
| 16 | —Cl | —Cl | —C(=O)—CH₂—CH₃ | —C(=O)—CH₂—CH₃ |
| 17 | —Cl | —Cl | —C(=O)—(CH₂)₂—CH₃ | —H |
| 18 | —Cl | —Cl | —C(=O)—(CH₂)₂—CH₃ | —C(=O)—(CH₂)₂—CH₃ |

TABLE 2-continued

| Ex. No. | X | Y | R' | R'' |
|---|---|---|---|---|
| 19 | —Cl | —Cl | $-\overset{O}{\overset{\|}{C}}-\underset{\underset{C_2H_5}{\|}}{CH}-(CH_2)_3-CH_3$ | —H |
| 20 | —Cl | —Cl | $-\overset{O}{\overset{\|}{C}}-\underset{\underset{C_2H_5}{\|}}{CH}-(CH_2)_3-CH_3$ | $-\overset{O}{\overset{\|}{C}}-\underset{\underset{C_2H_5}{\|}}{CH}-(CH_2)_3-CH_3$ |
| 21 | —Cl | —Cl | $-\overset{O}{\overset{\|}{C}}-\underset{\underset{OH}{\|}}{CH}-\underset{\underset{OH}{\|}}{CH}-\overset{O}{\overset{\|}{C}}-OH$ | —H |
| 22 | —Cl | —Cl | $-\overset{O}{\overset{\|}{C}}-\underset{\underset{OH}{\|}}{CH}-\underset{\underset{OH}{\|}}{CH}-\overset{O}{\overset{\|}{C}}-OH$ | $-\overset{O}{\overset{\|}{C}}-\underset{\underset{OH}{\|}}{CH}-\underset{\underset{OH}{\|}}{CH}-\overset{O}{\overset{\|}{C}}-OH$ |
| 23 | —Cl | —Cl | $-\overset{O}{\overset{\|}{C}}-\underset{\underset{OH}{\|}}{CH}-\underset{\underset{OH}{\|}}{CH}-\overset{O}{\overset{\|}{C}}-$ | |

EXAMPLES 24-33

Also by way of examples for practicing the present invention, the compounds according to Examples 24-33 having the formula

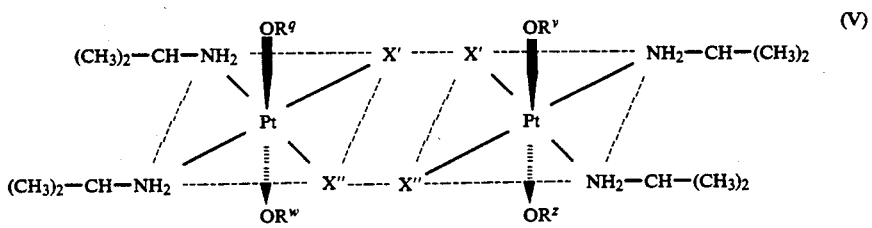

which are substituted as listed below at Table 3 can be produced by substantially following the above outlined procedures to react the appropriate carboxylic acid derivatives with appropriate axial-dihydroxy platinium complexes to yield compounds of Examples 24-33.

TABLE 3

| Ex. No. | X' | X'' | R$^q$ | R$^v$ | R$^w$ | R$^z$ |
|---|---|---|---|---|---|---|
| 24 | —Cl | —Cl | $-\overset{O}{\overset{\|}{C}}-\underset{\underset{NH_2}{\|}}{CH}-CH_2-\overset{O}{\overset{\|}{C}}-$ | —H | —H | |
| 25 | —Cl | —Cl | $-\overset{O}{\overset{\|}{C}}-\underset{\underset{NH_2}{\|}}{CH}-CH_2-\overset{O}{\overset{\|}{C}}-$ | $-\overset{O}{\overset{\|}{C}}-OH$ | —H | |
| 26 | —Cl | —Cl | $-\overset{O}{\overset{\|}{C}}-\underset{\underset{NH_2}{\|}}{CH}-CH_2-\overset{O}{\overset{\|}{C}}-$ | $-\overset{O}{\overset{\|}{C}}-OH$ | $-\overset{O}{\overset{\|}{C}}-OH$ | |
| 27 | —Cl | —Cl | $-\overset{O}{\overset{\|}{C}}-\underset{\underset{NH_2}{\|}}{CH}-CH_2-\overset{O}{\overset{\|}{C}}-$ | $-\overset{O}{\overset{\|}{C}}-\underset{\underset{NH_2}{\|}}{CH}-CH_2-\overset{O}{\overset{\|}{C}}-$ | | |
| 28 | —Cl | —Cl | $-\overset{O}{\overset{\|}{C}}-\underset{\underset{NH_2}{\|}}{CH}-(CH_2)_2-\overset{O}{\overset{\|}{C}}-$ | —H | —H | |
| 29 | —Cl | —Cl | $-\overset{O}{\overset{\|}{C}}-\underset{\underset{NH_2}{\|}}{CH}-(CH_2)_2-\overset{O}{\overset{\|}{C}}-$ | $-\overset{O}{\overset{\|}{C}}-\underset{\underset{NH_2}{\|}}{CH}-(CH_2)_2-\overset{O}{\overset{\|}{C}}-$ | | |
| 30 | —Cl | —Cl | $-\overset{O}{\overset{\|}{C}}-\underset{\underset{OH}{\|}}{CH}-\underset{\underset{OH}{\|}}{CH}-\overset{O}{\overset{\|}{C}}-$ | —H | —H | |
| 31 | —Cl | —Cl | $-\overset{O}{\overset{\|}{C}}-\underset{\underset{OH}{\|}}{CH}-\underset{\underset{OH}{\|}}{CH}-\overset{O}{\overset{\|}{C}}-$ | $-\overset{O}{\overset{\|}{C}}-\underset{\underset{OH}{\|}}{CH}-\underset{\underset{OH}{\|}}{CH}-\overset{O}{\overset{\|}{C}}-$ | | |

TABLE 3-continued

| Ex. No. | X' | X" | R$^q$ | R$^v$ | R$^w$ | R$^z$ |
|---|---|---|---|---|---|---|
| 32 | —Cl | —Cl | $-\overset{O}{\overset{\|}{C}}-\overset{OH}{\overset{\|}{CH}}-CH_2-\overset{OH}{\overset{\|}{CH}}-\overset{O}{\overset{\|}{C}}-$ | —H | —H | |
| 33 | —Cl | —Cl | $-\overset{O}{\overset{\|}{C}}-\overset{OH}{\overset{\|}{CH}}-CH_2-\overset{OH}{\overset{\|}{CH}}-\overset{O}{\overset{\|}{C}}-$ | | $-\overset{O}{\overset{\|}{C}}-\overset{OH}{\overset{\|}{CH}}-CH_2-\overset{OH}{\overset{\|}{CH}}-\overset{O}{\overset{\|}{C}}-$ | |

EXAMPLES 34–46

Also by way of examples for practicing the present invention, the compounds according to Examples 34–46 having the formula

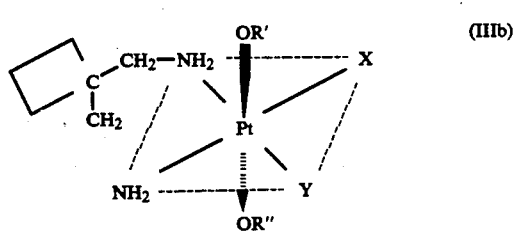
(IIIb)

which are substituted as listed below at Table 4 can be produced by substantially following the above outlined procedures to react the appropriate carboxylic acid derivatives with appropriate axial-dihydroxy platinum complexes to yield compounds of Examples 34–46.

TABLE 4

| Ex. No. | X | Y | R' | R" |
|---|---|---|---|---|
| 34 | —Cl | —Cl | $-\overset{O}{\overset{\|}{C}}-H$ | —H |
| 35 | —Cl | —Cl | $-\overset{O}{\overset{\|}{C}}-H$ | $-\overset{O}{\overset{\|}{C}}-H$ |
| 36 | —Cl | —Cl | $-\overset{O}{\overset{\|}{C}}-CH_3$ | —H |
| 37 | —Cl | —Cl | $-\overset{O}{\overset{\|}{C}}-CH_3$ | $-\overset{O}{\overset{\|}{C}}-CH_3$ |
| 38 | —Cl | —Cl | $-\overset{O}{\overset{\|}{C}}-CH_2-CH_3$ | —H |
| 39 | —Cl | —Cl | $-\overset{O}{\overset{\|}{C}}-CH_2-CH_3$ | $-\overset{O}{\overset{\|}{C}}-CH_2-CH_3$ |
| 40 | —Cl | —Cl | $-\overset{O}{\overset{\|}{C}}-(CH_2)_2-CH_3$ | —H |
| 41 | —Cl | —Cl | $-\overset{O}{\overset{\|}{C}}-(CH_2)_2-CH_3$ | $-\overset{O}{\overset{\|}{C}}-(CH_2)_2-CH_3$ |
| 42 | —Cl | —Cl | $-\overset{O}{\overset{\|}{C}}-\underset{C_2H_5}{\overset{\|}{CH}}-(CH_2)_3-CH_3$ | —H |
| 43 | —Cl | —Cl | $-\overset{O}{\overset{\|}{C}}-\underset{C_2H_5}{\overset{\|}{CH}}-(CH_2)_3-CH_3$ | $-\overset{O}{\overset{\|}{C}}-\underset{C_2H_5}{\overset{\|}{CH}}-(CH_2)_3-CH_3$ |
| 44 | —Cl | —Cl | $-\overset{O}{\overset{\|}{C}}-\overset{OH}{\overset{\|}{CH}}-\overset{OH}{\overset{\|}{CH}}-\overset{O}{\overset{\|}{C}}-OH$ | —H |
| 45 | —Cl | —Cl | $-\overset{O}{\overset{\|}{C}}-\overset{OH}{\overset{\|}{CH}}-\overset{OH}{\overset{\|}{CH}}-\overset{O}{\overset{\|}{C}}-OH$ | $-\overset{O}{\overset{\|}{C}}-\overset{OH}{\overset{\|}{CH}}-\overset{OH}{\overset{\|}{CH}}-\overset{O}{\overset{\|}{C}}-OH$ |

TABLE 4-continued

| Ex. No. | X | Y | R' | R" |
|---|---|---|---|---|
| 46 | —Cl | —Cl | | —C(O)—CH(OH)—CH(OH)—C(O)— |

EXAMPLES 47–59

Also by way of examples for practicing the present invention, the compounds according to Examples 47–59 having the formula

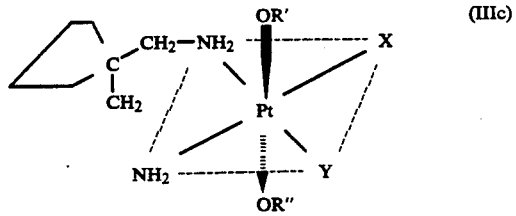

which are substituted as listed below at Table 5 can be produced by substantially following the above outlined procedures to react the appropriate carboxylic acid derivatives with appropriate axial di-hydroxy platinum complexes to yield compounds of Examples 47–59.

TABLE 5

| Ex. No. | X | Y | R' | R" |
|---|---|---|---|---|
| 47 | —Cl | —Cl | —C(O)—H | —H |
| 48 | —Cl | —Cl | —C(O)—H | —C(O)—H |
| 49 | —Cl | —Cl | —C(O)—CH$_3$ | —H |
| 50 | —Cl | —Cl | —C(O)—CH$_3$ | —C(O)—CH$_3$ |
| 51 | —Cl | —Cl | —C(O)—CH$_2$—CH$_3$ | —H |
| 52 | —Cl | —Cl | —C(O)—CH$_2$—CH$_3$ | —C(O)—CH$_2$—CH$_3$ |
| 53 | —Cl | —Cl | —C(O)—(CH$_2$)$_2$—CH$_3$ | —H |
| 54 | —Cl | —Cl | —C(O)—(CH$_2$)$_2$—CH$_3$ | —C(O)—(CH$_2$)$_2$—CH$_3$ |
| 55 | —Cl | —Cl | —C(O)—CH(C$_2$H$_5$)—(CH$_2$)$_3$—CH$_3$ | —H |
| 56 | —Cl | —Cl | —C(O)—CH(C$_2$H$_5$)—(CH$_2$)$_3$—CH$_3$ | —C(O)—CH(C$_2$H$_5$)—(CH$_2$)$_3$—CH$_3$ |
| 57 | —Cl | —Cl | —C(O)—CH(OH)—CH(OH)—C(O)—OH | —H |
| 58 | —Cl | —Cl | —C(O)—CH(OH)—CH(OH)—C(O)—OH | —C(O)—CH(OH)—CH(OH)—C(O)—OH |

TABLE 5-continued

| Ex. No. | X | Y | R' | R" |
|---|---|---|---|---|
| 59 | —Cl | —Cl | | —C(=O)—CH(OH)—CH(OH)—C(=O)— |

EXAMPLES 60-72

Also by way of examples for practicing the present invention, the compounds according to Examples 60-72 having the formula

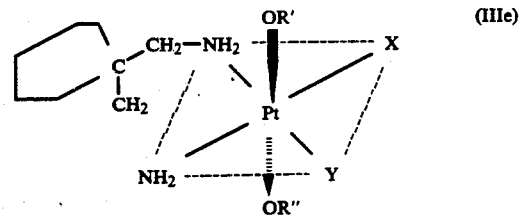
(IIIe)

which are substituted as listed below at Table 6 can be produced by substantially following the above outlined procedures to react the appropriate carboxylic acid derivatives with appropriate axial di-hydroxy platinum complexes to yield compounds of Examples 60-72.

TABLE 6

| Ex. No. | X | Y | R' | R" |
|---|---|---|---|---|
| 60 | —Cl | —Cl | —C(=O)—H | —H |
| 61 | —Cl | —Cl | —C(=O)—H | —C(=O)—H |
| 62 | —Cl | —Cl | —C(=O)—CH$_3$ | —H |
| 63 | —Cl | —Cl | —C(=O)—CH$_3$ | —C(=O)—CH$_3$ |
| 64 | —Cl | —Cl | —C(=O)—CH$_2$—CH$_3$ | —H |
| 65 | —Cl | —Cl | —C(=O)—CH$_2$—CH$_3$ | —C(=O)—CH$_2$—CH$_3$ |
| 66 | —Cl | —Cl | —C(=O)—(CH$_2$)$_2$—CH$_3$ | —H |
| 67 | —Cl | —Cl | —C(=O)—(CH$_2$)$_2$—CH$_3$ | —C(=O)—(CH$_2$)$_2$—CH$_3$ |
| 68 | —Cl | —Cl | —C(=O)—CH(C$_2$H$_5$)—(CH$_2$)$_3$—CH$_3$ | —H |
| 69 | —Cl | —Cl | —C(=O)—CH(C$_2$H$_5$)—(CH$_2$)$_3$—CH$_3$ | —C(=O)—CH(C$_2$H$_5$)—(CH$_2$)$_3$—CH$_3$ |
| 70 | —Cl | —Cl | —C(=O)—CH(OH)—CH(OH)—C(=O)—OH | —H |
| 71 | —Cl | —Cl | —C(=O)—CH(OH)—CH(OH)—C(=O)—OH | —C(=O)—CH(OH)—CH(OH)—C(=O)—OH |

TABLE 6-continued

| Ex. No. | X | Y | R' | R'' |
|---|---|---|---|---|
| 72 | —Cl | —Cl | | —C(=O)—CH(OH)—CH(OH)—C(=O)— |

The above compounds and procedures are merely illustrative of the invention, which invention is not limited to the compounds and procedures set forth above. Other examples of equivalent procedures and compounds will be apparent to one of ordinary skill in the art upon considering the above illustrative examples in view of that which is known to one of ordinary skill in this art. Accordingly, such equivalent procedures and compositions are within the scope of the invention and claims.

In Vitro and In Vivo Tests

Representative compounds of the invention were tested in in vitro cytotoxicity assay and in vivo tumor models according to procedures set forth above. The result of these evaluations are presented in Tables 7–10.

TABLE 7

IN VITRO CYTOTOXICITY

| COMPOUND | IC50 (micrograms/milliter) | |
|---|---|---|
| | B16 | HCT116 |
| Cisplatin | 5.4–7.3 | 4.2–4.5 |
| Iproplatin | 66.8–243 | 20.2–31.2 |
| Example 1 | 5.6 | 11 |
| Example 3 | 5 | 3.2 |
| Example 4 | 5.5 | 6.2 |
| Example 5 | 5.3 | 1.6 |
| Example 6 | 15.2 | 12.8 |
| Example 8 | NT | 0.3 |
| Example 9[a] | NT | NT |

NT = Not Tested
[a]Oil soluble, thus not tested in vitro.

Inhibition of L210 Murine Leukemia

Table 8 contains a summary of the evaluations for some of the example compounds for antitumor activity against L1210 murine leukemia. Listed for each compound is the maximum percent T/C achieved and the dose producing that effect.

TABLE 8

INHIBITION OF L1210 MURINE LEUKEMIA

| COMPOUND | MAXIMUM % T/C | DOSE[a] |
|---|---|---|
| A. Intraperitoneal Implanted Tumor | | |
| Cisplatin | 143–207 | 8–10 |
| Iproplatin | 143–171 | 40 |
| Example 1 | 136 | 40 |
| Example 3 | 164 | 32 |
| Example 4 | 143 | 60 |
| Example 5 | 143 | 16 |
| Example 6 | 129 | 40 |
| Example 8 | 143 | 16 |
| Example 9 | 100 | 120 |
| B. Intracerebral Implanted Tumor | | |
| Cisplatin | 114 | 10 |
| Iproplatin | 157 | 40 |
| Example 3 | 129 | 60 |
| Example 4 | 114 | 60 |

[a]Dose is in milligrams/kilogram administered intraperitoneally 1 time on Day 1 for the mice having an intraperitoneal implanted tumor and on Day 3 for the mice having the intracerebrally implanted tumor.

Inhibition of M5076 Sarcoma

The results of testing for some of the platinum complexes according to the present invention are summarized in Table 9 which lists the maximum percent T/C and T-C achieved by each complex and the dose producing that effect.

TABLE 9

INHIBITION OF M5076 SARCOMA

| COMPOUND | TREATMENT ROUTE | MAXIMUM % T/C | DOSE[a] | MAXIMUM T-C (Days) | DOSE[a] |
|---|---|---|---|---|---|
| Cisplatin | ip[a] | 126 | 4.8 | 33 | 4.8 |
| | iv[a] | 114–126 | 3.6–4.8 | 25–27.3 | 4.8 |
| Iproplatin | ip | 160+[b] | 48 | 34.5 | 36 |
| Example 3 | ip | 140 | 24 | 38.5+ | 24 |
| Example 4 | ip | 97 | 36 | 29.6 | 36 |
| Example 5 | iv | 124 | 16 | 16.3 | 24 |

[a]Dose is milligrams/kilogram, which is administered on Days 5, 9, 13, and 17, wherein "ip" and "iv" represent intraperitoneal and intravenous administration, respectively.
[b]Long term survivors with tumor.

Inhibition of P388 Murine Leukemia

The results of testing for some of the platinum complexes according to the present invention are summarized in Table 10 which lists the maximum percent T/C achieved by each complex and the dose producing that effect.

TABLE 10

INHIBITION OF P388 LEUKEMIA

| COMPOUND | TREATMENT | MAXIMUM % T/C | DOSE[a] |
|---|---|---|---|
| Cisplatin | | 173 | 12 |
| Example 1 | | 127 | 120 |
| Example 3 | | 144 | 96 |
| Example 5 | | 167 | 120 |

[a]Dose is milligrams/kilogram, which is administered orally (by gavage) 1 time on Day 1.

What is claimed is:
1. A compound of the formula

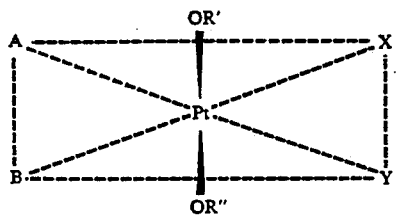

wherein A and B are each independently ammine or monodentate amine, or A and B taken together represent a bidentate amine, and A and B are coordinated to the platinum atom through their nitrogen atom; X and Y are each independently halogen; R' is $C_1$-$C_{20}$ alkanoyl, aroyl, heteroaroyl, or a group selected from the group consisting of

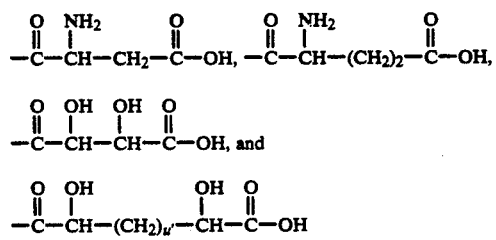

wherein u' is an integer from 1 to 5; and R" is hydrogen with the proviso that A, B, X, and Y are structurally equatorial substituents with respect to OR'-Pt-OR".

2. A compound according to claim 1 wherein R', is $C_1$-$C_{20}$ alkanoyl, aroyl or heteroaroyl, with the proviso that A,B, X and Y are structurally equatorial substituents with respect to OR'-Pt-OR".

3. A compound according to claim 1 where A and B each independently represent a group selected from the group consisting of ammine $C_3$-$C_7$ alicyclic amine, and $C_1$-$C_6$ straight or branched chain amine; or A and B are taken together to form a $C_3$-$C_7$ alkyl group, or a bis-(aminomethyl) $C_3$-$C_7$ cycloalkyl group; and R' is $C_1$-$C_{20}$ alkanoyl, aroyl or heteroaroyl.

4. A compound according to claim 2 wherein R' is $C_1$-$C_{10}$ alkanoyl.

5. A compound according to claim 3 wherein R' is $C_1$-$C_{10}$ alkanoyl.

6. A compound according to claim 4 wherein A and B taken together represent 1,2-diaminocyclohexane.

7. A compound according to claim 6 wherein the 1,2-diaminocyclohexane amine is as cis-, trans (d,l)-, trans (1- or trans (d).

8. A compound according to claim 4 wherein A and B each represent isopropylamine.

9. A compound according to claim 8 where R' is selected from the group consisting of formyl, acetyl, propionyl, butyryl, and 2ethylhexanoyl.

10. A compound according to claim 4 having the formula

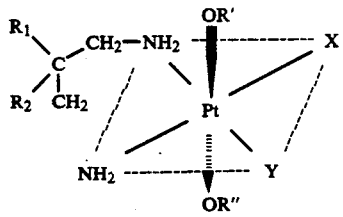

in which $R_1$ and $R_2$ each independently represent a hydrogen atom, $C_1$-$C_6$ alkyl, $C_3$-$C_7$ cycloalkyl, $C_6$-$C_{10}$ aryl or $C_6$-$C_{10}$ aryl-$C_1$-$C_6$ alkyl, or $R_1$, $R_2$ taken together with the carbon atom to which they are attached represent $C_3$-$C_7$ cycloalkyl.

11. A compound according to claim 10 wherein $R_1$ and $R_2$ each represent $CH_3$-$CH_2$— or wherein $R_1$, $R_2$ taken together with the carbon atom to which they are attached

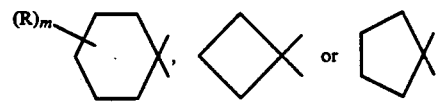

wherein each R is independently halogen or $C_1$-$C_6$ alkyl and m is an integer from 0 to 10.

12. A compound according to claim 10 wherein $R_1$, $R_2$ taken together with the carbon atom to which they are attached represent cyclohexyl.

13. A compound according to claim 12 wherein R'0 is acetyl, and X and Y each represent chloro.

14. A compound according to claim 4, having the formula

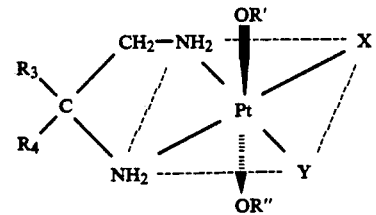

wherein $R_3$ and $R_4$ each represent $C_1$-$C_6$ alkyl or $R_3$, $R_4$ taken together with the carbon atom to which they are attached represent $C_3$-$C_6$ cycloalkyl.

15. A compound according to claim 4 wherein X and Y are both chloro; A and B taken together represent propanediamine.

16. A method for therapeutically treating an animal host affected by a malignant tumor which comprises administering to said host an effective tumor-inhibiting dose of a compound according to claim 1.

17. A pharmaceutical composition which comprises a pharmaceutically effective amount of a compound according to claim 1 in combination with an inert pharmaceutically acceptable carrier or diluent.

* * * * *